(12) United States Patent
Shen et al.

(10) Patent No.: US 7,943,733 B2
(45) Date of Patent: May 17, 2011

(54) SPACERS TO INCREASE THE EXPRESSION OF RECOMBINANT FUSION PROTEINS

(75) Inventors: Wei-Chiang Shen, San Marino, CA (US); Nurmamet Amet, Northridge, CA (US); Xiaoying Chen, Alhambra, CA (US); Hsin-Fang Lee, Alhambra, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 12/340,391

(22) Filed: Dec. 19, 2008

(65) Prior Publication Data

US 2009/0170163 A1 Jul. 2, 2009

Related U.S. Application Data

(60) Provisional application No. 61/015,580, filed on Dec. 20, 2007.

(51) Int. Cl.
C07K 1/00 (2006.01)
(52) U.S. Cl. ...................................................... 530/350
(58) Field of Classification Search .................. 530/350
See application file for complete search history.

(56) References Cited

U.S. PATENT DOCUMENTS

| | | | |
|---|---|---|---|
| 6,548,249 | B1 | 4/2003 | Anderson et al. |
| 6,551,795 | B1 | 4/2003 | Rubenfield et al. |
| 6,562,617 | B1 | 5/2003 | Anderson et al. |
| 6,936,421 | B2 | 8/2005 | Anderson et al. |
| 7,517,684 | B2 | 4/2009 | Rubenfield et al. |
| 2003/0143562 | A1 | 7/2003 | Anderson et al. |
| 2007/0020624 | A1 | 1/2007 | Rubenfield et al. |
| 2009/0042777 | A1 | 2/2009 | Shen et al. |

FOREIGN PATENT DOCUMENTS

WO 2005034877 A2 4/2005

OTHER PUBLICATIONS

Subramanian, et al., Albinterferon alpha-2b: a genetic fusion protein for the treatment of chronic hepatitis C. Nat. Biotechnol. 25: 1411-1419 (2007).
Pyror, et al., High-level expression of soluble protein in *Escherichia coli* using a His6-Tag and maltos-bindingprotein double-affinity fusion system. Protein Expr. Purif. 10:309-319 (1997).
Maeda, et al., Engineering of functional chimeric protein Gvargula luciferase. Anal. Biochem. 249: 147-152 (1997).
Arai, et al., Design of the linkers which effectively separate domains of a bifunctional fusion protein. Protein Eng. 14: 529-532 (2001).
Bai, et al., Improving the oral efficacy of recombinant granulocyte colony-stimulating factor and transferrin fusion protein by space optimization. Pharm. Res. 23: 2116-2121 (2006).
Jullien, et al., Regulation of Cre recombinase by ligand-induced complementation of inactive fragments. Nucleic Acids Res 31: e131 (2003).
Maeda, et al., A bifunctional poly(ethylene glycol) hybrid of lamininrelated peptides. Biochem Biophys Res Commun 248: 485-9 (1998).
Bai, et al., Recombinant granulocyte colony-stimulating factor-transferrin fusion protein as an oral myelopoietic agent. Proc. Natl. Acad. Sci.102: 7292-7296 (2005).
International search report for corresponding PCT application PCT/US08/87721 lists the references above.

*Primary Examiner* — Maryam Monshipouri
(74) *Attorney, Agent, or Firm* — DLA Piper LLP (US)

(57) ABSTRACT

The present invention relates to fusion proteins. The invention specifically relates to compositions and methods of Tf-based fusion proteins that demonstrate a high-level expression of transferrin (Tf)-based fusion proteins by inserting a helical linker between two protein domains.

6 Claims, 3 Drawing Sheets

SPACERS TO INCREASE THE EXPRESSION OF RECOMBINANT FUSION PROTEINS

The present application claims the benefit of the filing date of U.S. Provisional Application No. 61/015,580 filed Dec. 20, 2007, the disclosure of which is incorporated herein by reference in its entirety.

STATEMENT OF FEDERALLY SPONSORED RESEARCH AND DEVELOPMENT

The present invention is made, at least in part, with the support of grants from National Institute of Health (Grant R01 GM063647). The government has certain rights in the invention.

FIELD OF THE INVENTION

The present invention relates in general to fusion proteins. In particular, it relates to compositions and methods for increasing fusion protein expression using alpha-helical spacers.

BACKGROUND OF THE INVENTION

Recombinant proteins are becoming an important class of therapeutic drugs (1, 2). Many recombinant proteins such as growth hormones and humanized monoclonal antibodies are already in clinical uses (3). One of the limitations for the production of therapeutic proteins in biotech industry is the low yield of the recombinant proteins in cell culture systems. Various approaches have been taken to improve the expression and production of recombinant proteins from transfected mammalian cells, such as the selection of mutants (4), the use of virus-transfected cells (5), or the improvement of the culture medium (6). However, these conventional methods suffer from various shortcomings. For example, the use of mutants means that only certain mutants meeting the expression requirement may be used. This limits the range of proteins that may be expressed. The choice of virus-transfected cells and culture medium are also trial-and-error processes that require laborious experimentations to optimize the conditions. Moreover, they don't always solve problems caused due to structural features of the desired protein.

High quantities of recombinant proteins ranging from hundreds of milligrams to grams must be produced in order to carry out preclinical evaluations and clinical trials (7-9). Unfortunately, potential therapeutic proteins with poor expression face an obstacle to make it through clinical trials to final approval by the FDA. Protein therapeutics developed from recombinant hormones, growth factors and cytokines express at relatively low levels, not only increasing the manufacturing cost but also delaying further product evaluation. Some successful protein therapeutics are recombinant fusion proteins consisting of cytokines or growth factors fused with the Fc portion of IgG1 or immunotoxin and are expressed as single polypeptides with dual biological activities (10,11). These therapeutic fusion proteins, including Enbrel® (TNF-R/Fc-IgG1), Ontak® (IL-2/diphtheria toxin), Orencia® (CTLA-4/Fc-IgG1) and Amevive® (LFA-3/Fc-IgG1) (12), may experience poor expression as the fusion partners interfere with each other for optimal translation, especially in mammalian cells. Since mammalian cells are the preferred choice for producing some therapeutic proteins, as posttranslational modifications in these cells may be associated with reduced immunogenicity compared to other systems (9), a simple strategy that enhances the expression of therapeutic fusion proteins in mammalian cells would be desirable.

Typically, the problem of low expression is improved by incorporating carbohydrate-binding module (CBM) and maltose-binding protein (MBP) as fusion partners to the target protein (13,14). However, these fusion partners are generally removed during or after purification by introducing peptide linkers with cleavage sites for endopeptidases such as thrombin and factor Xa (14). Conceivably, this approach is not feasible for large-scale production of target proteins because it requires numerous steps of column purification and enzymatic processing, limiting the production capacity and possibly causing non-specific cleavage.

The selection of a peptide linker with the ability to maintain domain function of the fusion protein is becoming important (15-18). Recently, the inventors designed a helical linker with 50 amino acids using an EAAAK (SEQ ID NO: 3) helix-forming motif based on a previous study (16), and inserted the linker between granulocyte colony stimulating factor (G-CSF) and Tf moieties, leading to increased biological activity (19). Most recently, the inventors found that the insertion of the same helical linker in Tf-fusion proteins resulted in a high-level expression in HEK293 cells as compared to the same fusion proteins without the helical linker. Here the inventors report the helical linker-dependent increase of expression in two Tf-based fusion proteins, G-CSF and human growth hormone (hGH), and provide evidence of a high-level of expression for both proteins regardless the level of original expression without the linker. Conceivably, this approach can be introduced and applied to other fusion proteins with limited to no expression, greatly improving the production yield for downstream applications.

The above-mentioned and other features of this invention and the manner of obtaining and using them will become more apparent, and will be best understood, by reference to the following description, taken in conjunction with the accompanying drawings. The drawings depict only typical embodiments of the invention and do not therefore limit its scope.

SUMMARY OF THE INVENTION

In one embodiment, the invention relates to fusion proteins comprising a helical linker between the protein domains and has an increased level of expression in a vector as compared to fusion proteins without a linker between the protein domains.

In accordance with another embodiment, the invention relates to compositions comprising fusion proteins comprising a helical linker between the protein domains.

In a closely related embodiment, the invention relates to helical linkers that allow for a high level of expression in a vector and improved bioactivity of fusion proteins, when the linkers are inserted between the protein domains.

In another embodiment, the invention relates to methods of making fusion proteins comprising a helical linker inserted between the protein domains.

In yet another embodiment, the invention relates to methods using helical linkers to increase the transfection of fusion protein vectors and the production of the fusion protein, in a cellular expression system.

DETAILED DESCRIPTION

Figures 1, 2:
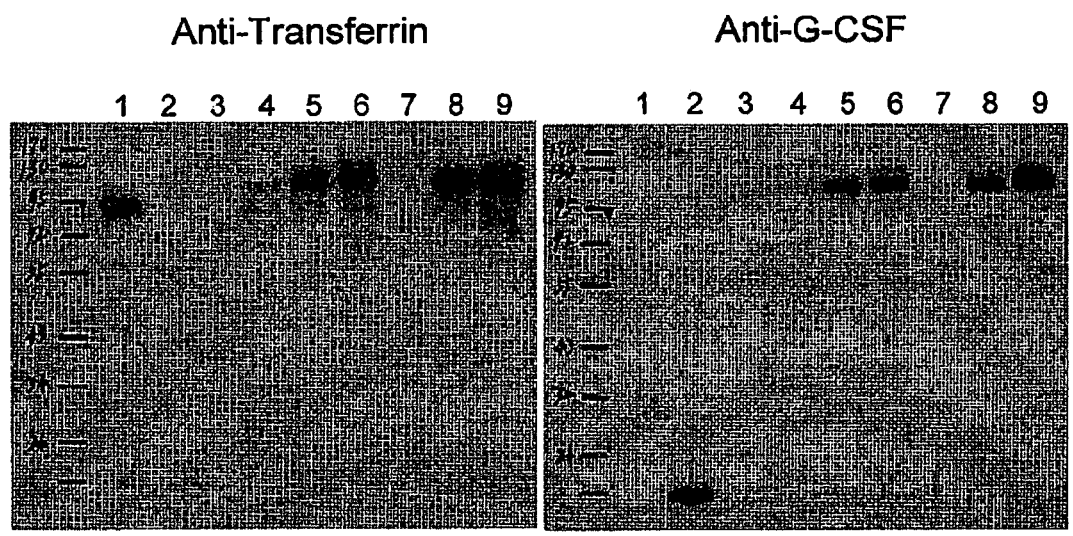
FIG. 1. Oligonucleotide insert of the H4 linker and its corresponding amino acid sequence.
FIG. 2. Comparison of the expression of various fusion proteins using Western blotting. Lane 1: 50 ng Transferrin; Lane 2: 50 ng G-CSF; Lane 3: transfected with pcDNA3.1; Lane 4: transfected with pcDNA3.1-sTf-G-CSF; Lane 5: transfected with pcDNA3.1-sTf-H41-G-CSF; Lane 6: transfected with pcDNA3.1-sTf-H42-G-CSF; Lane 7: transfected with pcDNA3.1-sTf-H42R-G-CSF (H42 with a reverse sequence); Lane 8: transfected with pcDNA3.0-sGCSF-Tfxx (LE); Lane 9: transfected with pcDNA3.0-sGCSF-H4(2)-Tfxx.

Recently, a peptide linker, A(EAAAK)$_n$A, (SEQ ID No: 4), has been reported to form an alpha-helix conformation, which is able to control the distance and reduce the interference between the domains of a recombinant protein (20). It was reported that the helix linker could effectively separate bifunctional domains of the fusion protein (21,22). The inventors of the present invention have previously demonstrated that the intrinsic bioactivity of the fusion protein can be optimized by the insertion of alpha-helical spacers between G-CSF and Tf domains (23). In this invention, the inventors have further discovered that insertion of the alpha-helical spacers can increase either transfection or production of the fusion protein. Accordingly, based on the discoveries of the present invention, the inventors have devised methods for enhancing and optimizing transfection of fusion protein vectors and the production of the fusion protein, in a cellular expression system.

As used herein the term "fusion protein" refers to or describes a protein that comprises at least two protein domains that are separated by one or more helical linkers. The helical linker may be EAAAK (SEQ ID NO: 5) based. Examples of proteins that may used in the "fusion protein" include but are not limited to carrier proteins such as transferrin, serum albumin, an antibody or sFv, and the like, and therapeutic proteins such as interferon, colony stimulating factor (CSF), interferon, a cytokine, a hormone, a lymphokine, an interleukin, a hematopoietic growth factor, a toxin, and the like. The fusion proteins may be expressed in a variety of host cells, including human kidney cells, E. Coli, bacteria, yeast, and various higher eukaryotic cells such as the COS, CHO, HeLa and myeloma cell lines, and the like. More preferably, the fusion protein comprises at least one carrier protein and a therapeutic protein.

Materials and Methods

Preparation of Gene Fusion Constructs in pcDNA3.1(+)

Fusion constructs for Tf-based fusion proteins containing either hGH or human G-CSF were designed and established in the pcDNA3.1(+) (Invitrogen) mammalian expression vector based on a previous report (24). Briefly, the DNA sequences encoding for hGH or G-CSF were subcloned and fused in frame to the sequences encoding for Tf. The DNA sequences encoding for the signal peptide from the N-terminus domain were incorporated in the polypeptide; however, the stop codon from the N-terminus domain was deleted for uninterrupted translation. The final constructs were verified by DNA sequence analysis.

Helical Linker Insertion

Two domains between Tf and hGH or G-CSF in the fusion protein were fused by leucine (L) and glutamic acid (E), a product of XhoI restriction site. The helical linker, H4 and $(H4)_2$, LEA(EAAAK)$_4$ALE (SEQ ID NO: 1) and LEA (EAAAK)$_4$ALEA(EAAAK)$_4$ALE (SEQ ID NO: 2), respectively, were prepared and inserted according to the previous study (19). The orientation, sequences and copy numbers of the helical linker were confirmed by DNA sequence analysis.

Production of Fusion Protein

The human embryonic kidney 293 cells (HEK293 or HEK293T; ATCC) were cultured in DMEM media (Mediatech) containing 10% FBS, 50 units penicillin/50 µg streptomycin in a humidified incubator at 37° C. with 5% CO2. HEK293 cells were seeded at near confluence in six-well plates (Costar) and transiently transfected with 2 µg expression constructs and 5.5 µl Lipofectamine 2000 (Invitrogen). The transfected cells were allowed to express fusion proteins in serum free CD293 media (Invitrogen) for 5 days. The conditioned media containing the fusion protein was then harvested, clarified by centrifugation, and concentrated using Amicon Ultra-4 or Ultra-15 filtering devices (Millipore).

SDS-PAGE and Western Blots

The fusion proteins were fractionated on a 10% SDSPAGE or 4-20% pre-cast gel (Thermo Scientific) and visualized by staining with Coomassie blue. For Western blot analysis, the fusion proteins were transferred to a PVDF membrane (GE healthcare) and blocked with 5% non-fat milk for 1 h at room temperature, after separating on SDSPAGE. hGH and Tf were identified by using goat anti-hGH monoclonal antibody (1:1, 000; R&D Systems) and goat antihuman Tf antibody (1:5, 000) as primary antibodies and rabbit anti-goat antibody conjugated to HRP as secondary antibody. Likewise, the G-CSF was detected by using rabbit anti-human G-CSF (1:10,000) as primary antibody and donkey anti-rabbit antibody conjugated to HRP (1:10,000) as secondary antibody. All antibodies were obtained from Sigma, unless mentioned otherwise. ECL plus reagents (GE Healthcare) and ChemiDoc XBR (Bio-Rad) were used for developing and capturing the hGH-fusion proteins. X-ray film was used to develop G-CSF-fusion proteins. The expression of both hGH- and G-CSF-fusion proteins were analyzed using Quantity One software (Bio-Rad), and results from either anti-hGH or anti-G-CSF Western blots are comparable to that of anti-Tf Western blots.

In Vitro Cell Proliferation

Nb2 cells (Sigma) derived from rat T lymphoma cells were cultured as suspension in RPMI 1640 media (Mediatech) supplemented with 2 mM glutamine, 10% FBS, 10% horse serum (HS; Invitrogen), 50 units of penicillin/50 pg streptomycin, and 50 µM 2-mercaptoethanol (25) in a humidified incubator at 37° C. with 5% $CO_2$. For proliferation assays, Nb2 cells were washed extensively in a serum free RPMI 1640 media, re-suspended in assay media that included 10% HS but not FBS, and counted with a Z1 Coulter particle counter (Beckman Coulter). About 5,000 Nb2 cells per well were seeded into 96-well plates in 200 µl assay media, starved for 24 h, treated with hGH or fusion protein whose dose was normalized to that of hGH, and incubated for 4 days. Next, the cells were added with 20 µl of Alamar Blue dye (Biosource) and incubated overnight for color development. The TV absorbance was measured at 570 nm using a Genios spectrophotometer (Tecan) and corrected by subtracting the control without treatment. The ED50 was defined as the dose of fusion protein that led to half of maximum proliferation.

The following examples are intended to illustrate, but not to limit, the scope of the invention. While such examples are typical of those that might be used, other procedures known to those skilled in the art may alternatively be utilized. Indeed, those of ordinary skill in the art can readily envision and produce further embodiments, based on the teachings herein, without undue experimentation.

EXAMPLES

Comparison of the Expression Level of Tf-G-CSF and G-CSF-Tf Fusion Proteins with or without H4 Linker Construction of Plasmid Human G-CSF fused in frame with Tf was constructed into the expression vector pcDNA3.0. Three different peptide linkers were inserted between G-CSF and Tf as spacers: amino acid alpha-helical linker with 2 copies of A(EAAAK)$_4$A (H4)$_2$(SEQ ID NO: 4), a short LE dipeptide linker, and a linker with the reverse of oligonucleotide sequence of H4 to serve as a random peptide linker.

HEK293T Cell Transient Transfection

HEK293T cells grown in monolayer were transfected with the plasmids by Lipofectamine 2000. The fusion protein released into the 4-day conditioned medium was collected.

Comparison of the Expression Level of Tf-H4n-G-CSF (n=0-2) Fusion Protein

Plasmids with various copies of the H4 linker were transfected into HEK293T cells to produce the fusion proteins. Cells were seeded into 6-well culture plate 1 day prior to transfection. 2 µg of each plasmid was transfected into each well of cells. 96 hours after transfection, the medium was collected and centrifuged at 1500 rpm for 5 min. to remove cells. 20 µL of each sample is taken to perform Western Blotting.

FIG. 2 shows comparison of the expression of various fusion proteins by using Western blotting. The lanes in the blot are as follows:

|  | Expression Ratio |
|---|---|
| Lane 1: 50 ng Transferrin | |
| Lane 2: 50 ng G-CSF | |
| Lane 3: transfected with pcDNA3.1 | |
| Lane 4: transfected with pcDNA3.1-sTf-G-CSF | 1 |
| Lane 5: transfected with pcDNA3.1-sTf-H4$_1$-G-CSF | 7.83 |
| Lane 6: transfected with pcDNA3.1-sTf-H4$_2$-G-CSF | 11.20 |
| Lane 7: transfected with pcDNA3.1-sTf-H4$_2$R-G-CSP | 0 |
| Lane 8: transfected with pcDNA3.0-sGCSF-Tfxx (LE) | 10.75 |
| Lane 9: transfected with pcDNA3.0-sGCSF-H4(2)-Tfxx | 15.52 |

Results

The H4 linker boosted the expression level of Tf-G-CSF. It is believed that this effect may be achieved through increasing the stability of the fusion protein. The expression level of Tf-G-CSF fusion protein containing 2 copies of H4 linker (FIG. 2, lane 6) is higher than that of Tf-G-CSF containing 1 copy of H4 linker (FIG. 2, lane 5) which, in turn, is higher than that of TfG-CSF without linker (FIG. 2, lane 4). Similarly, the expression level of G-CSF-Tf containing 2 copies of H4 linker (FIG. 2, lane 9) is higher than that of a short dipeptide LE linker (FIG. 2, lane 8). There was no expression of the fusion protein when the inserted oligonucleotide was (H4)$_2$ in reverse sequence, (H4)$_2$R (FIG. 2, lane 7). Since the reverse sequence will generate a peptide spacer with random conformation, this finding suggests that an alpha-helical structure in the spacer is required to promote the expression and production of the fusion protein.

Gene Fusion Constructs

To investigate whether the insertion of a helical linker between the protein domains in the Tf-based fusion protein improves the expression, the inventors constructed three pairs of gene fusion plasmids with or without the inserted helical linker, and confirmed that the insertion, orientation and number of copies were correct. Subsequently, the plasmid constructs were transfected to HEK293 or HEK293T cells to produce fusion proteins.

Comparison of hGH-Tf and hGH-(H4)$_2$-Tf Fusion Proteins for Expression

Figure 3:
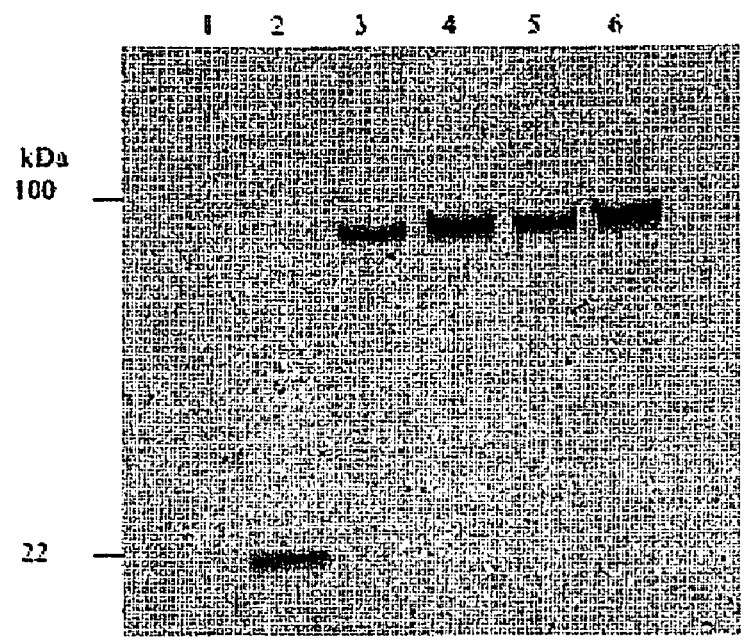
FIG. 3. High-level expression by the insertion of helical linker in both hGH-Tf and Tf-hGH fusion proteins as analyzed by Anti-hGH Western blot. Four fusion proteins with or without the inserted helical linker, expressed in serum free media, were analyzed by Western blot using goat anti-hGH monoclonal antibody (1:1,000). The signal was detected using HRP-conjugated rabbit anti-goat secondary antibody (1:1,000) and ECL reagents. The image was recorded and analyzed by ChemiDoc XBR (Bio-Rad). Lane 1: Tf (negative control); lane 2: hGH (10 ng); lane 3: hGH-Tf; lane 4: hGH-$(H4)_2$-Tf; lane 5: Tf-hGH; lane 6: Tf-(H4)2-hGH.
Figure 4:
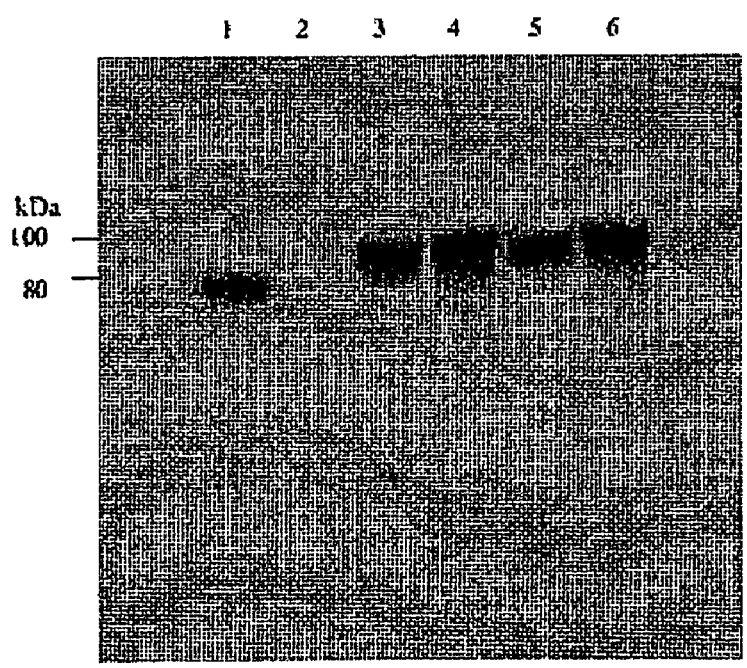
FIG. 4. High-level expression by the insertion of helical linker in both hGH-Tf and Tf-hGH fusion proteins as analyzed by Anti-Tf Western blot. Four fusion proteins with or without the inserted helical linker, expressed in serum free media, were analyzed by Western blot using goat anti-Tf antibody (1:5,000). The signal was detected using rabbit anti-goat secondary antibody conjugated to HRP (1:1,000) and ECL reagents. The image was recorded and analyzed by ChemiDoc XBR. Lane 1: Tf (50 ng); lane 2: hGH (negative control); lane 3: hGH-Tf, lane 4: hGH-$(H4)_2$-Tf, lane 5: Tf-hGH; lane 6: Tf-$(H4)_2$-hGH.
Figure 5:
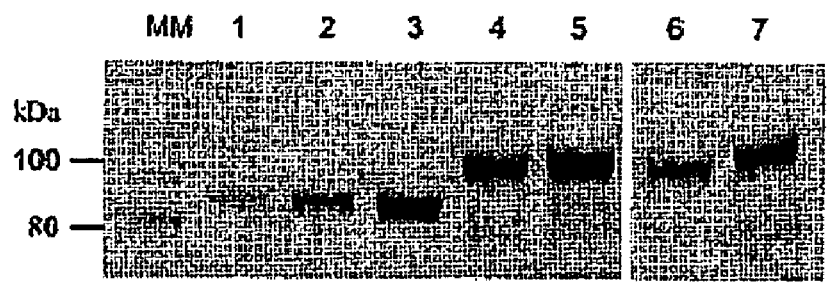
FIG. 5. Helical linker insertion led to high-level expression in both hGH-Tf and Tf-hGH fusion protein as analyzed by SDS-PAGE. Same volume of conditioned media (5 µl) from the transfected HEK-293 cells were fractionated using SDS-PAGE, stained with Coomassie blue, and analyzed with ChemiDoc XBR. MM: molecular weight marker; lanes 1-3: Tf control; lane 4: hGH-Tf; lane 5: hGH-$(H4)_2$-Tf; lane 6: Tf-hGH; lane 7: Tf-$(H4)_2$-hGH.

The hGH-Tf fusion protein consists of human growth hormone and Tf linked by a short di-peptide linker; whereas the hGH-(H4)$_2$-Tf fusion protein is linked by a helical linker with 50 amino acids. To assess the level of expression, the fusion proteins with or without the helical linker were analyzed by Western blot as well as SDS-PAGE with Coomassie stain. Both anti-hGH and anti-Tf Western blots detected a band corresponding to approximately 100 kDa, which is the sum of molecular weights from Tf (79 kDa) and hGH (22 kDa), and confirmed that the fusion protein was composed of two moieties including Tf and hGH (FIG. 4, lanes 3 and 4). To evaluate and compare the level of expression, band-densities for each fusion protein were quantified and analyzed. The density data revealed that the fusion protein with the helical linker expressed at a level 1.7 fold higher than the original fusion protein without the helical linker (Table I, FIG. 3, lanes 3 and 4). In addition, fusion proteins were analyzed by SDSPAGE stained with Coomassie blue to confirm results from the band-density analysis from Western blots, and to evaluate relative purity and abundance. The results from SDS-PAGE demonstrated that the fusion proteins were expressed with high purity (~90%) and high abundance (~95%) at a molecular weight of 100 kDa (FIG. 5, lane 5). Furthermore, band-density analysis from Coomassie blue-stained SDSPAGE showed that the expression of fusion protein with the helical linker was about 1.7 fold higher than the original fusion protein without the helical linker (FIG. 5, lane 4), confirming results from Western blot analysis.

Comparison of Tf-hGH and Tf-(H4)$_2$-hGH Fusion Proteins for Expression

Thus far, the fusion proteins evaluated were oriented to have a N-terminal hGH domain and C-terminal Tf domain. To investigate the effect of the helical linker on the expression of fusion proteins with different orientation, the Tf- and hGH-domains were switched to produce two new fusion proteins: Tf-hGH and Tf-(H4)2-hGH. The two fusion proteins were expressed and the yield of expression was compared. The Western blot data with fusion protein specific antibodies including anti-hGH and anti-Tf confirmed the identity and molecular weight (100 kDa) of the fusion protein, as well as the insertion of helical linker as shown by slightly increased molecular weight (FIG. 3, lanes 5 and 6, FIG. 4, lanes 5 and 6). The band-density analysis from Western blot data showed the fusion protein with the inserted helical linker expressed at a higher level with a ~2.4 fold increase as compared to the original fusion protein without the helical linker (Table I). The SDS-PAGE with Coomassie stain revealed that both fusion proteins were expressed with high purity (~90%) and high abundance (90%) but the fusion protein with the helical linker expressed at high levels with a ~2.4 fold increase compared to the original fusion protein without the helical linker (FIG. 5, lane 7 and 6, respectively), further confirming the Western blot data.

Comparison of Tf-G-CSF and Tf-(H4)2-G-CSF Fusion Proteins for Expression

Figure 6:
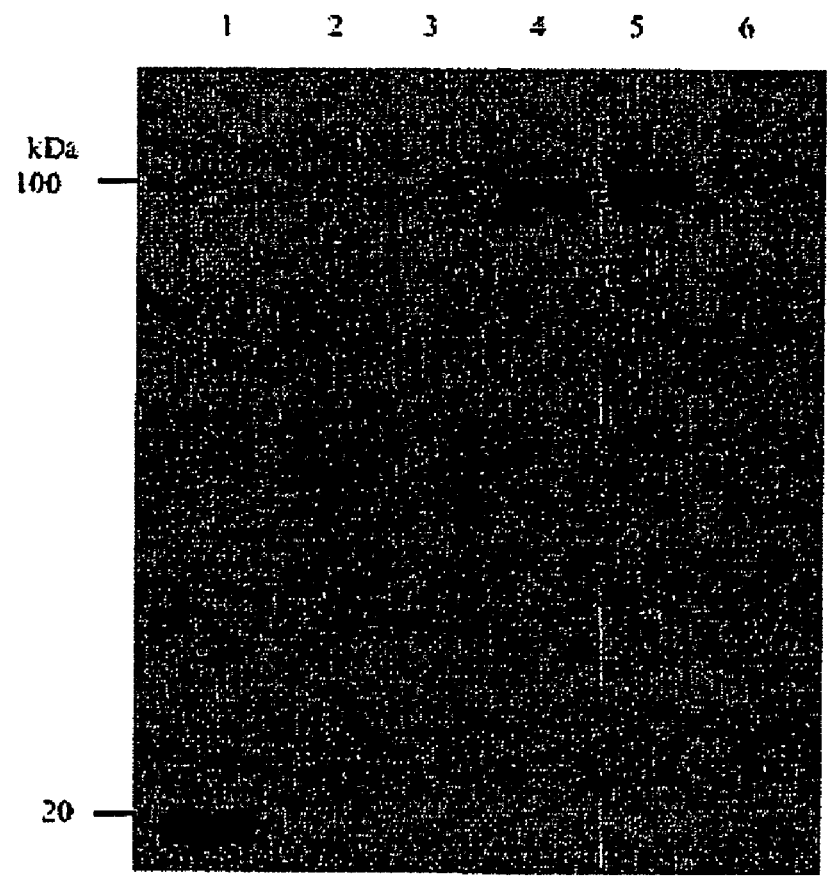
FIG. 6. Helical linker insertion led to high-level expression in both GCSF-Tf and Tf-G-CSF fusion protein as analyzed by anti-G-CSF Western blot. Fifteen-microliter-conditioned media from the transfected HEK-293 cells were analyzed using anti-GCSF Western blot. Lane 1: G-CSF control; lane 2: pcDNA3.1(+) without the insert; lane 3: Tf-G-CSF; lane 4: Tf-(H4)-G-CSF; lane 5: Tf-$(H4)_2$-G-CSF; lane 6: Tf-r$(H4)_2$-G-CSF (fusion protein with a reversed (H4)2 DNA sequence inserted, thus a non-helical linker in the product).

To study the broader implication of the helical linker insertion on the increased expression of Tf-based fusion proteins, Tf-G-CSF fusion protein consisting of transferrin and granulocyte colony-stimulating factor was constructed, and subsequently, the helical linker was inserted. These two fusion proteins were expressed to compare the level of expression. The Western blot using anti-G-CSF antibody detected a 100-kDa band equivalent to the molecular weight of Tf-G-CSF fusion protein (~80+19 kDa), confirming the identity and molecular weight (FIG. 6). Moreover, the Western blot data revealed that the expression from the Tf-G-GSF fusion protein was too low to detect convincingly (FIG. 6, lane 3). In contrast, the Tf-(H4)-G-CSF and Tf-(H4)$_2$-G-CSF fusion proteins expressed at elevated levels with a 7.8 and an 11.2 fold increase as compared to original fusion protein without the linker, respectively, providing notable evidence for the improved expression of Tf-based fusion proteins by the insertion of a helical linker (FIG. 6, lanes 4 and 5, Table I). The fusion protein expressed with a reversed coding sequence for the helical linker (Tf-r(H4)$_2$-G-CSF) failed to express (FIG. 6, lane 6). Taken together, the helical linker insertion between Tf and G-CSF domains led to a significant increase in expression, comparing with the original fusion protein without the helical linker.

Comparison of In Vitro Cell Proliferation

The hGH-(H4)$_2$-Tf and Tf-(H4)$_2$-hGH fusion proteins were tested in vitro to determine whether they induce Nb2 cell proliferation. The Nb2 cells treated with either hGH-(H4)$_2$-Tf or Tf-(H4)$_2$-hGH fusion protein demonstrated higher proliferation activity as compared to Nb2 cells treated with the hGHTf fusion protein without helical linker (Table II).

TABLE I

The Ratio of Expression of Tf-fusion Proteins with or without the Helical Linker

| Linker (x) | G-CSF Fusion Proteins | | hGH Fusion Proteins | |
| --- | --- | --- | --- | --- |
| | Tf-x-G-CS | G-CSF-x-Tf | Tf-x-hGH | hGH-x-Tf |
| No Liker | 1 | 1 | 1 | 1 |
| H4 | 7.8 | ND | ND | ND |
| (H4)$_2$ | 11 | 1.44 | 2.39 | 1.66 | x - linker inserted between Tf and hGH or G-CSF;
(H4)$_2$ - two copies of helical linker;
no linker - two domains were fused by LE peptide;
ND—not determined.

TABLE II

Comparing Nb2 Proliferation Activity of hGH-Tf Fusion Protein, with or without the Helical Linker ED50(ng/mL)

| Linker (x) | hGH | hGH-x-Tf | Tf-x-hGH |
| --- | --- | --- | --- |
| No Liker | 0.25 | 1.85 | NA$^a$ |
| (H4)$_2$ | — | 0.85 | 0.80 |

$^a$Was not determined due to low yield of the fusion protein

Discussion

The success of constructing biologically active recombinant G-CSF-Tf fusion protein with the helical linker (19,24) led us to pursue the feasibility of producing other Tf fusion proteins. To achieve this goal, the inventors constructed recombinant fusion protein consisting of Tf and hGH, and introduced two copies of a helical linker (H4)2 as a spacer between two protein domains. As previously reported in G-CSF fusion protein (19), the insertion of the helical linker also increases the in vitro biological function of hGH fusion protein as shown in the Nb2 cell proliferation assay (Table II).

Besides the increase of in vitro biological activity, the inventors found that the expression level of both fusion proteins with the helical linker, i.e., G-CSF-(H4)$_2$-Tf and hGH-(H4)$_2$-Tf, was significantly higher than that of fusion proteins without the linker. The inventors further investigated the effect of helical linker insertion on the expression of fusion proteins with a Tf domain switch, i.e., Tf-(H4)$_2$-G-CSF and Tf-(H4)$_2$-hGH, which created a fusion protein with a different orientation. As shown in FIGS. 5 and 6, the expression of the fusion protein with Tf at the amino-terminus is generally very poor. However, the insertion of the helical linker significantly increased the expression of both fusion proteins with Tf at the amino-terminus (Table I).

The inventors have reported previously that the expression of GCSF-Tf fusion protein failed when a flexible and non-helical linker, consisting of glycine and serine (GSSSS)3 (SEQ ID NO: 6), was inserted between Tf and G-CSF domains (19). Others have also found that the insertion of IgG hinge region as a flexible linker between Tf and nerve growth factor (NGF) domains was ineffective for the expression of this fusion protein (18). To further demonstrate the requirement of the helical structure of the linker peptide for the increase of the fusion protein expression, the inventors reversed the DNA sequence coding for the helical peptide to produce a linker with an identical peptide length, but a non-helical structure. Our results showed that there was no expression of the fusion protein, Tf-r(H4)$_2$-GCSF (FIG. 6, lane 6). These findings led us to the conclusion that the increase of the expression of Tf-based fusion protein is due to the non-flexible and helical nature of the linker that is inserted between the two protein domains.

The exact mechanism responsible for this increased expression is unclear. However, the rigid, extended nature, as well as the composition, of the helical linker may help increase the rate of hGH- and Tf-domain folding. A proper folding will enhance the stability of the newly translated polypeptide and, consequently, will increase the expression of Tf fusion proteins in the conditioned media. By using fluorescent resonance energy transfer (FRET) technique, Arai et al. found that the insertion of a helical linker between the enhanced green fluorescent protein (EGFP) domain and enhanced blue fluorescent protein (EBFP) domain in a chimeric protein increased the distance and kept two domains apart (16). Furthermore, Robinson and Sauer (26) reported that the composition and length of linker between two domains were important in controlling the rate of folding, unfolding, and stability of chimeric protein. It is likely that a large molecule, such as Tf-G-CSF or Tf-hGH fusion protein with a molecular weight of 100 kDa, requires large conformational space to fold correctly. The stable and efficient folding may drive the equilibrium towards an increased expression and accumulation of the fusion protein. Conceivably, the linker with a helical structure can hold the domains at a distance, providing a larger space for correct folding.

Another possible reason for the increased expression is that a helical linker with its secondary structure may be resistant to enzymatic cleavage by protecting the target amino acids from protease recognition, thereby increasing overall stability of the fusion protein (27). Further studies that evaluate the stability of the helical linker against common proteolytic enzymes including trypsin and chymotrypsin, would aid partially in our understanding of the mechanisms responsible for the increased expression.

In general, a high level expression of fusion proteins may be achieved: (1) by designing expression vectors with strong promoters and episomal origins; (2) by transfecting host cells such as HEK293T and HEK293 EBNA1 with expression of episomal antigens including SV40 large-T antigen and EBV nuclear antigen, respectively; (3) by selecting transfection reagents with highest gene transfer efficiency; and (4) by developing or using culture media with enhanced cell proliferation and survival but with minimum cell death and apoptosis (7-9). Furthermore, the addition of sodium butyrate and peptone into the culture media containing the transfected cells can have positive effect on the expression of target protein. However, long-term consequences of using such components in culture media remain controversial and unknown (28,29). Results in this report demonstrate that a high level expression of Tf-fusion proteins can be achieved by the insertion of a helical peptide linker between the two protein domains. If the increase of expression can be demonstrated in fusion proteins other than Tf, it will provide a simple and practical technique to improve the production of recombinant fusion proteins for therapeutic and diagnostic uses.

CONCLUSIONS

The inventors found that the insertion of a helical peptide as the linker in Tf-based fusion proteins led to a high level of expression, with superior in vitro bioactivity. This approach provides a simple method to increase poor expression of other fusion proteins. Given the straightforward approach and ease of both designing and introducing the helical linker in the fusion protein, this qualifies as a feasible strategy for the production of therapeutic fusion proteins at high levels in mammalian cells.

Methods according to the present invention can be easily adapted for currently established cell culture systems for recombinant protein production, without changing either the cell types or the culture conditions.

Many modifications and variation of the invention as hereinbefore set forth can be made without departing from the spirit and scope thereof and therefore only such limitations should be imposed as are indicated by the appended claims.

All patent and literature references cited in the present specification are hereby incorporated by reference in their entirety.

REFERENCES

1. J. M. Reichert and C. Paquette. Therapeutic recombinant proteins: trends in US approvals 1982 to 2002. Curr Opin Mol Ther 5: 139-47 (2003).

2. J. M. Reichert and C. Paquette. Clinical development of therapeutic recombinant proteins. Biotechniques 35: 176-8, 180, 182-5 (2003).

3. L. M. Weiner. Fully human therapeutic monoclonal antibodies. J Immunother 29: 1-9 (2006).

4. R. J. Kaufman. Selection and coamplification of heterologous genes in mammalian cells. Methods Enzymo/185: 537-566 (1990).

5. R. B. DuBridge, P. Tang, H. C. Hsia, P. M. Leong, J. H. Miller and M. P. Calos. Analysis of mutation in human cells by using an Epstein-barr virus shuttle system. Mol. Cell. Biol 7: 379-387 (1987).

6. P. L. Pham, S. Perret, B. Cass, E. Carpentier, G. St-Laurent, L. Bisson, A. Kamen and Y. Durocher. Transient gene expression in HEK293 cells: peptone addition post-transfection improves recombinant protein synthesis. Biotechnol Bioeng 90: 332-344 (2005).

7. L. Baldi, D. L. Hacker, M. Adam, and F. M. Wurm. Recombinant protein production by large-scale transient gene expression in mammalian cells: state of the art and future perspectives. Biotechnol. Lett. 29:677-684 (2007).

8. F. Wurm, and A. Bernard. Large-scale transient expression in mammalian cells for recombinant protein production. Curr. Opin. Biotechnol. 10:156-159 (1999).

9. F. M. Wurm. Production of recombinant protein therapeutics in cultivated mammalian cells. Nat. Biotechnol. 22:1393-1398 (2004).

10. G. M. Subramanian, M. Fiscella, A. Lamousé-Smith, S. Zeuzem, and J. G. McHutchison. Albinterferon alpha-2b: a genetic fusion protein for the treatment of chronic hepatitis C. Nat. Biotechnol. 25:1411-1419 (2007).

11. C. Wu, H. Ying, C. Grinnell, S. Bryant, R. Miller, A. Clabbers, S. Bose, D. McCarthy, R. R. Zhu, and L. Santora. Simultaneous targeting of multiple disease mediators by a dual-variable domain immunoglobulin. Nat. Biotechnol. 25:1290-1297 (2007).

12. B. Leader, Q. J. Baca, and D. E. Golan. Opinion: protein therapeutics: a summary and pharmacological classification. Nature Reviews Drug Discovery. 7:21-39 (2008).

13. M. Kavoosi, A. L. Creagh, D. G. Kilburn, and C. A. Haynes. Strategy for selecting and characterizing linker peptides for CBM9-tagged fusion proteins expressed in *Escherichia coli*. Biotechnol. Bioeng. 98:599-610 (2007).

14. K. D. Pryor, and B. Leiting. High-level expression of soluble protein in *Escherichia coli* using a His6-Tag and maltose-binding protein double-affinity fusion system. Protein Expr. Purif. 10:309-319 (1997).

15. Y. Maeda, H. Ueda, J. Kazami, G. Kawano, E. Suzuki, and T. Nagamune. Engineering of functional chimeric protein Gvargula luciferase. Anal. Biochem. 249:147-152 (1997).

16. R. Arai, H. Ueda, A. Kitayama, N. Kamiya, and T. Nagamune. Design of the linkers which effectively separate domains of a bifunctional fusion protein. Protein Eng. 14:529-532 (2001).

17. R. Arai, W. Wriggers, Y. Nishikawa, T. Nagamune, and T. Fujisawa. Conformations of variably linked chimeric proteins evaluated by synchrotron X-ray small-angle scattering. Proteins Structure Function and Bioinformatics. 57:829-838 (2004).

18. E. Park, R. M. Starzyk, J. P. McGrath, T. Lee, J. George, A. J. Schutz, P. Lynch, and S. D. Putney. Production and characterization of fusion proteins containing transferrin and nerve growth factor. J. Drug Target. 6:53-64 (1998).

19. Y. Bai, and W. C. Shen. Improving the oral efficacy of recombinant granulocyte colony-stimulating factor and transferrin fusion protein by spacer optimization. Pharm. Res. 23:2116-2121 (2006).

20. R. Arai, H. Ueda, A. Kitayama, N. Kamiya, and T. Nagamune. Design of the linkers which effectively separate domains of a bifunctional fusion protein. Protein Eng 14: 52932 (2001).

21. N. Jullien, F. Sampieri, A. Enjalbert, and J. P. Herman. Regulation of Cre recombinase by ligand-induced complementation of inactive fragments. Nucleic Acids Res 31: e131 (2003).

22. M. Maeda, K. Kawasaki, Y. Mu, H. Kamada, Y. Tsutsumi, T. J. Smith, and T. Mayumi. Amino acids and peptides. XXXIII. A bifunctional poly(ethylene glycol) hybrid of laminin related peptides. Biochem Biophys Res Commun 248: 485-9 (1998).

23. Y. Bai and we Shen. Improving the oral efficacy of recombinant granulocyte colony stimulating factor and transferring fusion protein by spacer optimization. Pharm Res 23: 2116-2121 (2006).

24. Y. Bai, D. K. Ann, and W.-C. Shen. Recombinant granulocyte colony-stimulating factor-transferrin fusion protein as an oral myelopoietic agent. Proc. Natl. Acad. Sci. 102:7292-7296 (2005).

25. M. Ishikawa, A. Nimura, R. Horikawa, N. Katsumata, O. Arisaka, M. Wada, M. Honjo, and T. Tanaka. A novel specific bioassay for serum human growth hormone. J. Clin. Endocrinol. Metab. 85:4274-4279 (2000).

26. C. R. Robinson, and R. T. Sauer. Optimizing the stability of single-chain proteins by linker length and composition mutagenesis. Proc. Natl. Acad. Sci. 95:5929-5934 (1998).

27. S. Marqusee, and R. L. Baldwin. Helix stabilization by Glu-\cdots Lys+ salt bridges in short peptides of de novo design. Proc. Natl. Acad. Sci. U.S. A. 84:8898-8902 (1987).

28. P. L. Pham, S. Perret, B. Cass, E. Carpentier, G. St-Laurent, L. Bisson, A. Kamen, and Y. Durocher. Transient gene expression in HEK293 cells: peptone addition post-transfection improves recombinant protein synthesis. Biotechnol. Bioeng. 90:332-344 (2005).

29. C. K. Crowell, Q. Qin, G. E. Grampp, R. A. Radcliffe, G. N. Rogers, and R. I. Scheinman. Sodium butyrate alters erythropoietin glycosylation via multiple mechanisms. Biotechnol. Bioeng. 99:201-213 (2008).

---

What is claimed is:

1. A two-domain fusion protein construct for improving expression of a fusion protein having a first protein domain and a second protein domain, said construct comprising:
   an alpha-helical peptide linker inserted between said first and second domains of the fusion protein,
   wherein inclusion of said alpha-helical peptide linker in said fusion protein increases the expression level of said fusion protein as compared to fusion proteins comprising said two domains without said linker.

2. The fusion protein construct according to claim 1, wherein said alph-helical peptide linker comprises more than one helical motif between said first and second domains.

3. The fusion protein construct according to claim 1, wherein said alpha-helical peptide linker comprises LEA(EAAAK)$_4$ALE (SEQ ID NO: 1).

4. The fusion protein construct according to claim 1, wherein:
   said first protein domain comprises a carrier protein selected from the group consisting of a transferrin, a serum albumin, an antibody and sFv; and
   said second protein domain comprises a therapeutic protein selected from the group consisting of a colony stimulating factor (CSF), an interferon, a cytokine, a hormone, a lymphokine, an interleukin, a hematopoietic growth factor, and a toxin.

5. The fusion protein construct according to claim 4, wherein said second protein domain comprises a granulocyte colony stimulating factor (G-CSF) or a human growth hormone (hGH).

6. The fusion protein construct according to claim 1, wherein said first protein domain is a transferrin (Tf)-based protein domain.

* * * * *

SEQUENCE LISTING

```
<160> NUMBER OF SEQ ID NOS: 5

<210> SEQ ID NO 1
<211> LENGTH: 11
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(8)
<223> OTHER INFORMATION: residues 4 to 8 is repeated 4 times

<400> SEQUENCE: 1

Leu Glu Ala Glu Ala Ala Ala Lys Ala Leu Glu
1               5                   10

<210> SEQ ID NO 2
<211> LENGTH: 20
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (4)..(8)
<223> OTHER INFORMATION: residues 4 to 8 are repeated 4 times
<220> FEATURE:
<221> NAME/KEY: MISC_FEATURE
<222> LOCATION: (13)..(17)
<223> OTHER INFORMATION: residues 13 to 17 are repeated 4 times

<400> SEQUENCE: 2

Leu Glu Ala Glu Ala Ala Ala Lys Ala Leu Glu Ala Glu Ala Ala Ala
1               5                   10                  15

Lys Ala Leu Glu
```

```
<210> SEQ ID NO 3
<211> LENGTH: 5
<212> TYPE: PRT
<213> ORGANISM: Artificial
<220> FEATURE:
<223> OTHER INFORMATION: Synthetic

<400> SEQUENCE: 3

Glu Ala Ala Ala Lys
1               5

<210> SEQ ID NO 4
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(6)
<223> OTHER INFORMATION: residues 2 to 6 are repeated 1 or more times

<400> SEQUENCE: 4

Ala Glu Ala Ala Ala Lys Ala
1               5

<210> SEQ ID NO 5
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(5)
<223> OTHER INFORMATION: residues 1 to 5 are repeated 3 times

<400> SEQUENCE: 5

Gly Ser Ser Ser Ser
1               5
```